US009301690B2

(12) United States Patent
Razavi et al.

(10) Patent No.: US 9,301,690 B2
(45) Date of Patent: Apr. 5, 2016

(54) DEVICE, SYSTEM, AND METHOD FOR A STRESS SENSING MEDICAL NEEDLE

(75) Inventors: Mehdi Razavi, Houston, TX (US); Gangbing Song, Pearland, TX (US); Alireza Nazeri, Houston, TX (US); Siu Chun Michael Ho, Sugar Land, TX (US)

(73) Assignees: UNIVERSITY OF HOUSTON SYSTEM, Houston, TX (US); TEXAS HEART INSTITUTE, Houston, TX (US)

(*) Notice: Subject to any disclaimer, the term of this patent is extended or adjusted under 35 U.S.C. 154(b) by 136 days.

(21) Appl. No.: 13/091,655

(22) Filed: Apr. 21, 2011

(65) Prior Publication Data

US 2011/0288405 A1 Nov. 24, 2011

Related U.S. Application Data

(60) Provisional application No. 61/326,808, filed on Apr. 22, 2010.

(51) Int. Cl.
*A61B 5/05* (2006.01)
*A61B 5/00* (2006.01)
*G01L 1/24* (2006.01)

(52) U.S. Cl.
CPC ............. *A61B 5/0084* (2013.01); *A61B 5/489* (2013.01); *A61B 5/6848* (2013.01); *G01L 1/243* (2013.01); *G01L 1/246* (2013.01); *A61B 2562/0233* (2013.01)

(58) Field of Classification Search
USPC .......... 600/423–424, 433–435, 466–467, 478
See application file for complete search history.

(56) References Cited

U.S. PATENT DOCUMENTS

| | | | |
|---|---|---|---|
| 4,794,931 A | 1/1989 | Yock | |
| 4,887,606 A | 12/1989 | Yock et al. | |
| 5,158,545 A * | 10/1992 | Trudell et al. | 604/509 |
| 5,311,871 A | 5/1994 | Yock | |
| 6,210,340 B1 * | 4/2001 | Amano et al. | 600/500 |
| 2003/0179998 A1 * | 9/2003 | Zhang et al. | 385/37 |
| 2004/0267340 A1 * | 12/2004 | Cioanta et al. | 607/105 |
| 2005/0070844 A1 * | 3/2005 | Chow et al. | 604/95.04 |
| 2005/0075704 A1 * | 4/2005 | Tu | A61B 18/245 607/88 |
| 2008/0255629 A1 * | 10/2008 | Jenson et al. | 607/19 |
| 2008/0285909 A1 * | 11/2008 | Younge et al. | 385/13 |

OTHER PUBLICATIONS

Vucevic, M., et al, "The SMART needle." 1994, Anesthesia, 49, pp. 889-891.
Abboud, P.A., et al. "Ultrasound guidance for vascular access." 2004, Emerg. Med. Clin. North Am., 22(3), pp. 749-773.
(Continued)

*Primary Examiner* — Joel F Brutus
(74) *Attorney, Agent, or Firm* — Winstead PC

(57) ABSTRACT

In an embodiment, an apparatus comprises a needle (e.g., hypodermic needle or trocar) and sensor (e.g., fiber Braggs grating sensor) coupled to a system to determine (e.g., in real time) stress and/or vibrations encountered by the needle. Consequently, various embodiments may (a) help identify nearby vessels, (b) determine whether the needle penetrated a hollow body structure, and (c) accurately guide needles towards a target structure (e.g., vessel). Other embodiments are described herein.

20 Claims, 10 Drawing Sheets

(56) References Cited

OTHER PUBLICATIONS

Randolph, A.G., et al., "Ultrasound guidance for placement of central venous catheters: a meta-analysis of the literature." 1996, Crit. Care Med., 24(12), pp. 2053-2058.

National Instruments, "Fundamentals of FBG Optical Sensing," Mar. 23, 2011, pp. 1-5.

National Instruments, "FBG Optical Sensing: A New Alternative for Challenging Strain Measurements," Apr. 19, 2011, pp. 1-4.

* cited by examiner

US 9,301,690 B2

DEVICE, SYSTEM, AND METHOD FOR A STRESS SENSING MEDICAL NEEDLE

This application claims priority to U.S. Provisional Patent Application No. 61/326,808 filed on Apr. 22, 2010 and entitled "A DEVICE AND SYSTEM FOR A STRESS AND VIBRATION SENSING MEDICAL NEEDLE", the content of which is hereby incorporated by reference.

BACKGROUND

Complications with vascular access include hematomas, pseudoanuerysms, retroperitoneal bleeding, and arteriovenous pseudoanuerysm. Causes for complications include: (1) difficulty in locating the entry site to the target vessel (e.g., artery or vein), and (2) inadvertent perforation or dissection of a wall (e.g., posterior wall) of the vessel into collateral structures (e.g., adjacent veins or the retroperitoneal space). Also, wire and sheath placement may further lead to such complications. Furthermore, attempts at hemostasis (e.g., manual or by closure devices) may assume direct, focal penetration of the needle at only one vessel site and consequently, may be unsuccessful.

Vessel prelocation methods for vascular access include the landmark technique, x-ray assistance, and ultrasound guidance. The landmark technique may be carried out through palpation and consideration of anatomical landmarks around the insertion site. Fluoroscopy, which uses x-ray scans to visualize the situation, may be used. Also, ultrasound may provide audible feedback to estimate the location of the needle in relation to the target vessel. However, ultrasound may require complicated training, may have limitations during hypotensive emergencies, can be expensive, and may suffer complications when used for the arterial system. Doppler needles have had limited success as well.

BRIEF DESCRIPTION OF THE DRAWINGS

Features and advantages of embodiments of the present invention will become apparent from the appended claims, the following detailed description of one or more example embodiments, and the corresponding figures, in which:

DETAILED DESCRIPTION

In the following description, numerous specific details are set forth but embodiments of the invention may be practiced without these specific details. Well-known circuits, structures and techniques have not been shown in detail to avoid obscuring an understanding of this description. "An embodiment", "example embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact. Also, while similar or same numbers may be used to designate same or similar parts in different figures, doing so does not mean all figures including similar or same numbers constitute a single or same embodiment.

In the following discussion "needle" means a shaft of essentially stiff material used to penetrate (i.e., pierce) the body, including but not limited to hypodermic needles, trocars, catheters, dilators, sheaths, and the like. Needles are included in many embodiments but other embodiments are not so limited and address conduits of varying flexibility (from very flexible to extremely rigid or stiff).

As described above, accidental puncture of vessels may cause morbid complications. Thus, knowing when a needle approaches a vessel increases the safety of vascular access procedures, whether the vessel is an artery, vein, or other hollow body structure. In an embodiment, an apparatus comprises a needle (e.g., hypodermic needle or trocar) and sensor (e.g., fiber Braggs grating sensor) coupled to a system to determine (e.g., in real time) stress encountered by the needle. Consequently, various embodiments may (a) help identify nearby vessels, (b) determine whether the needle penetrated a hollow body structure, (c) accurately guide needles towards a target structure (e.g., vessel); (d) clarify the difference between a vein and an artery during vascular access procedures (e.g., insertion of a catheter into a vein); (e) rapidly define a target artery to help decrease procedure time when treating obese or elderly patients (i.e., patients with sclerotic or otherwise tortuous vascular anatomy); and (f) provide immediate feedback that the user has exited or entered the wall of the vessel may lower the risk of hemoatomas, retroperitoneal hematomas, and pseudoaneurysms.

Figure 1A:
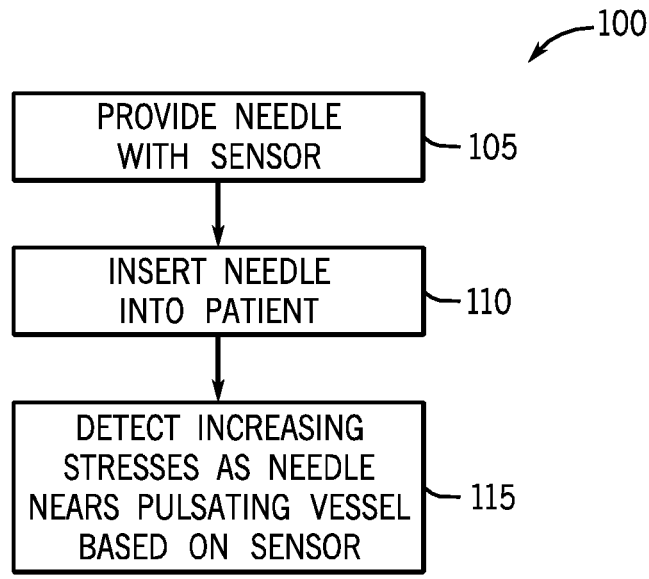
FIGS. 1a and 1b include methods in embodiments of the invention.
Figure 2:
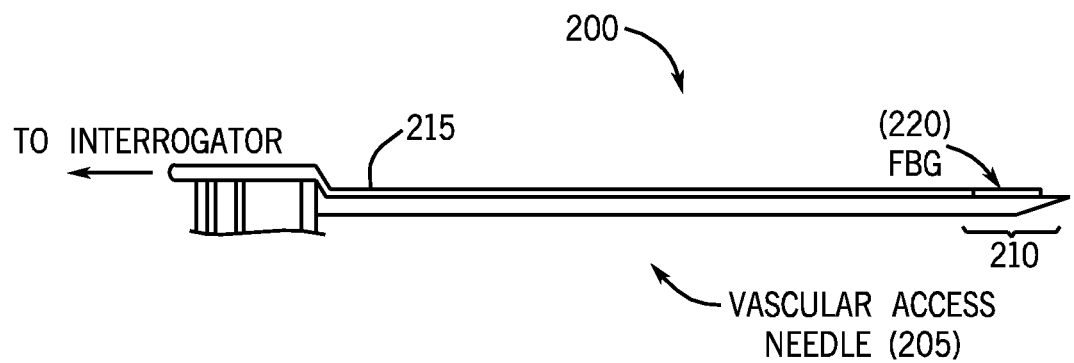
FIGS. 2 and 3 include embodiments of the invention.

FIG. 1A includes method 100 in an embodiment of the invention. Block 105 provides a rigid hollow needle having an end portion coupled to a fiber optic cable, a light source, and an optical sensing stress sensor. FIG. 2 includes an embodiment of such a device. Device 200 includes a rigid hollow needle 205, such as a vascular access needle. Needle 205 includes an inner channel to allow fluid transfer and/or equipment (e.g., catheters) access to patient vessels. Needle 205 has enough rigidity to enable a user to puncture the patient's skin and/or vessel wall with the needle. End portion 210 may include a sharpened tip to puncture the patient's skin and/or vessel wall. In the embodiment of FIG. 2, fiber optic cable 215 (FOC) couples to a light source (not shown) and optical sensing stress sensor 220. The FOC couples sensor 220 to an interrogator (not shown). Sensor 220 may be bonded to the needle's outer or inner surface or on a separate stylet to be inserted into the core of the needle during operation. Other embodiments are not so limited.

In block 110 a user inserts end portion 210 into a patient having a pulsating blood vessel (e.g., artery). Light is provided from the light source to FOC 215 and the user advances the end portion towards the pulsating blood vessel.

In block 115 the device detects increasing stresses, over a multi-second time period (e.g., time period it takes to puncture skin, move end portion near target vessel, and puncture target vessel) and in substantially real-time, based on both advancing end portion 210 towards the pulsating blood vessel and optically sensing with the with optical sensing stress sensor 220.

Figure 3:
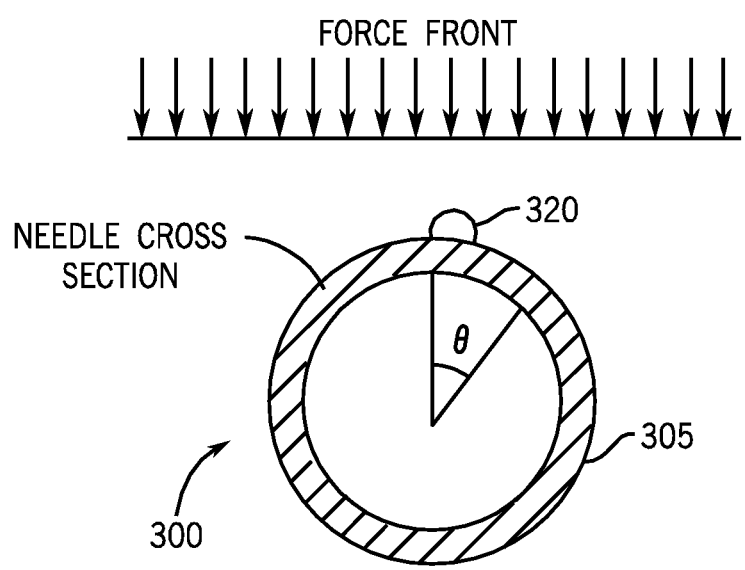

FIG. 3 includes an embodiment of device 300. In this embodiment (but not necessarily in other embodiments) sensor 320 includes a fiber Bragg grating (FBG) coupled to needle 305. FBGs may include a collection of reflective strips (i.e., grating) written into a small segment or portion of a FOC. As broadband light is directed into the fiber (from a light source coupled to the FOC) a wavelength will be reflected back towards the light source. The reflected wavelength has the same periodicity as the grating. As the physical spacing (i.e., the periodicity) of the grating changes due to externally induced stresses, the wavelength of the reflected light also changes. By measuring the reflected wavelength (e.g., from which the magnitude of wavelength change can be determined) the stress experienced by the FBG can be deduced.

As used herein, "stress" is an indicator of force and is not necessarily limited to strict definition of a measure of the internal forces acting within a deformable body or a measure of the average force per unit area of a surface within the body on which internal forces act. Stress, as used herein, reflects varying forces, strains, vibrations, and the like.

Thus, in block 115 a FBG sensor may detect increasing stresses by detecting changes in wavelength. These changes in stresses (and consequent changes in reflected wavelength) may be based on advancing end portion 210 (where sensor 220 is located in some embodiments) towards the pulsating blood vessel to sense the pulses from the blood vessel. Stresses are induced by stress (e.g., vibrations) propagated through various tissue mediums due to hemodynamic flow. These mediums may include various solids or semi-solids (e.g., adipose and muscular tissue). When the needle is inserted into the medium, the needle may deflect from these waves and vibrations. These deflections may not necessarily be seen by the eye and may not be strong enough to steer the needle towards any one direction. However, the stresses (e.g., strains) from these deflections are detectable by FBG sensors.

An embodiment including an optical sensor was constructed for 2D detection of pulses originating from an artificial circulatory system. The device successfully detected and registered the pulsatile motion of fluids through a flexible latex tube cast inside a block of tissue-like polymer. Specifically, an embodiment was tested for its ability to infer the direction of an incoming force, such as the propagation of an arterial pulse through tissue. Direction is defined as an angle θ with respect to the 360° rotation around the long or longitudinal axis of the needle.

the positions of the sensor or sensors (e.g., FBGs) around the needle cross section can be described by θ. For convenience, angular position of the impacting force at θ=0°. To set up a convention for FIG. 3, the incident angle between needle 305 and the force θ=0°. In other words, θ=0° is the angular position where the force of the pulse impends on the needle. This position may be actively calculated.

Signals to be detected will include forces impacting the sides of the needle. Two main positions of the needle were used in the example of FIG. 4. First, the needle was placed directly underneath and perpendicular to the tube. Second, the needle was pointed directly at the tube, but at an angle. An FBG with a center wavelength of 1556 nm was bonded to the distal end portion of an 18 G (OD×ID: 0.05×0.033") vascular access needle (approximately 88.19 mm long excluding the handle) by using epoxy. FBG 220, 320 had a span of 5 mm with its distal end situated about 6 mm before the tip of end portion 210. Signals from the FBG were read by an optical interrogator (Picowave) and displayed on a processor based system (e.g., laptop, PDA, Smartphone, desktop, cloud based system). Data was saved into a text file to be processed (e.g., using Excel, Matlab, and the like). In an embodiment, the needle may include a channel and the FOC and the sensor may both be included in the channel.

For the artificial vascular system, latex tubing was attached to a manually operated siphon pump to simulate the heart and a major artery (e.g., femoral artery). The initial two foot portion of the tubing (OD×ID: ½×⅛") was connected to smaller diameter (¼×⅛") tubing through a rigid plastic cylinder. The input port was attached to a tube leading to a tank of tap water. Each squeeze of the pump caused water to flow through the tubing circuit. Tissue simulant (e.g., Permagel) was cast over the distal end of the outflow tubing in order to imitate the passage of vascular tissue through muscle/fat. The experimental setup simulates stresses propagated through muscle/fat due to arterial pulsation.

Needle 305 was inserted into the tissue simulant around the tubing. Upon reaching a desired depth, the needle handle was fixed into place. The tubes leading into and out of the water tank were also secured to minimize vibrations. Several tests were carried out to characterize the FBG needle's ability to locate a pulsating blood vessel.

Figure 4:
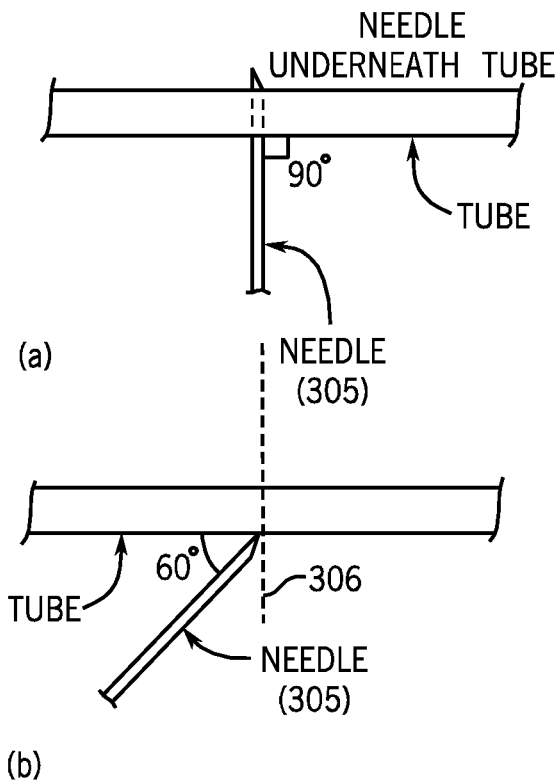
FIGS. 4-7 depict determining vessel location in an embodiment of the invention.

Again, FIG. 4 shows basic orientations for testing of one embodiment of the invention. In FIG. 4a needle 305 is shown underneath the tubing with FBG sensor (not shown) facing the surface of the tube. In FIG. 4b needle 305 is shown at a 30 degree incident angle with respect to normal axis 306. With these orientations in mind, a series of tests were conducted. The first test (FIG. 5) put the needle about 0.5 mm underneath and perpendicular to the tube (needle and FBG facing upwards, orthogonal to tube, and facing tube). The needle was then removed and reinserted approximately 5.0 mm below its initial position. This was done for up to 12.0 mm distance from the tube. Another test (FIG. 6) had the needle facing downwards (orthogonal to tube but facing away from tube such as may be the case if needle goes through both walls of a vessel). Still another test (FIG. 7) had the long axis of the needle parallel to the tube.

Figure 5:
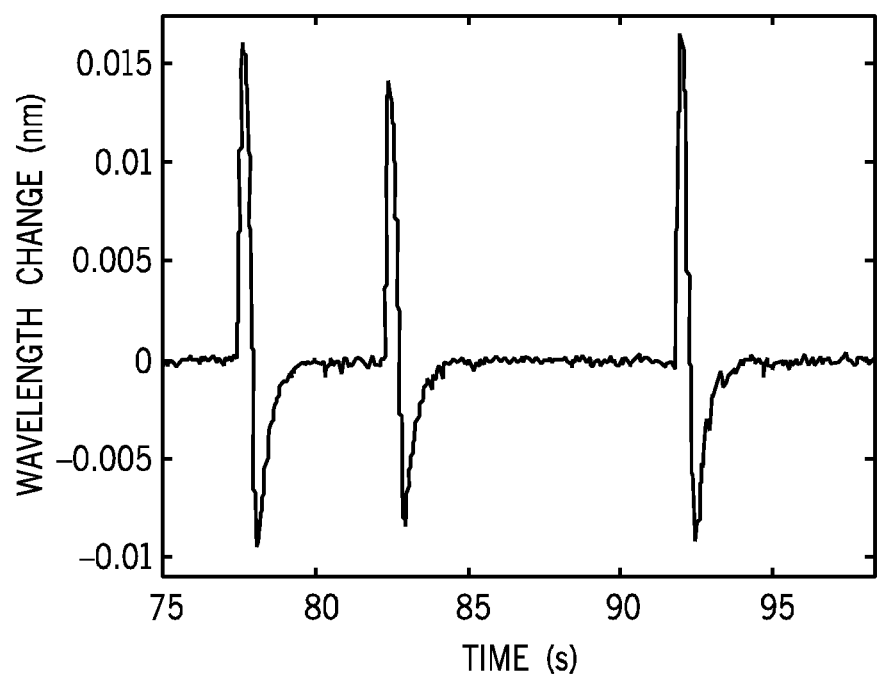
Figure 6:
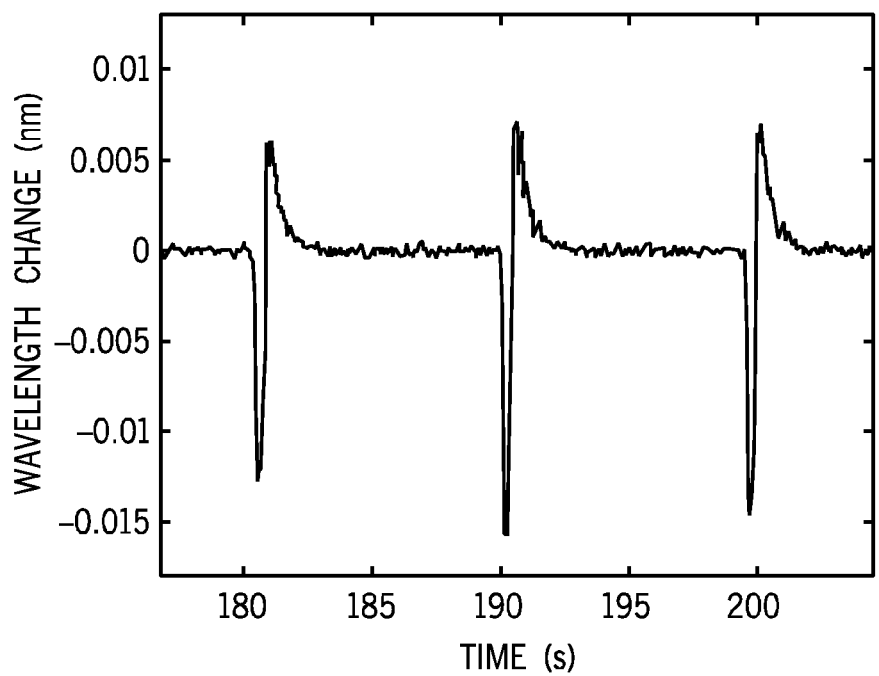
Figure 7:
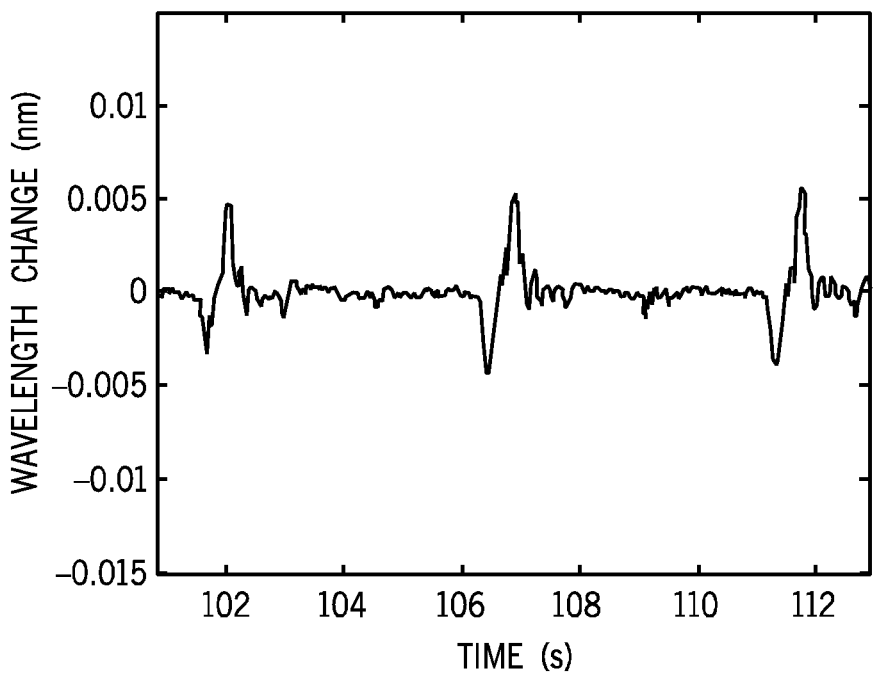

In FIG. 5, when the needle was underneath the pulsating tube maximum signals (0.015 nm wavelength change; average peak is 0.0153±0.0048 nm (n=15)) occurred when the FBG faced directly at the tube. When the FBG faced in a directly opposite direction (FIG. 6), the average wavelength changed negatively but with a similarly large magnitude (−0.01439 nm wavelength change; average peak: −0.01439±0.0031 nm (n=16)). In FIG. 7, the signal magnitude was minimum when the FBG faced 90 degrees from the artificial vessel (−0.0058 nm wavelength change; average peak: −0.0058±0.0032 nm (n=16)). The average peak value was highest when the FBG directly faced the tube (0.0153 nm).

Figure 9:
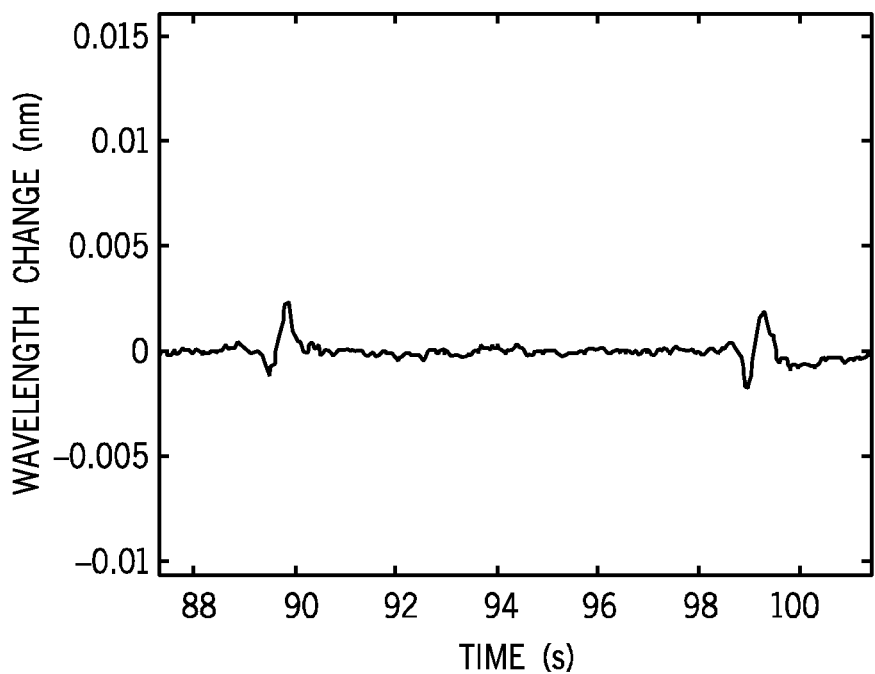
Figure 10:
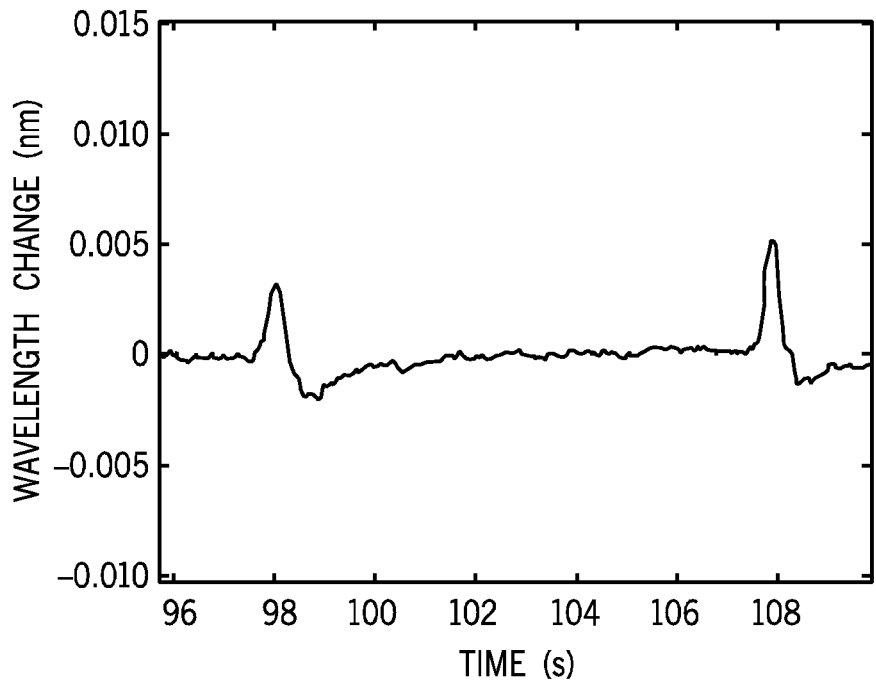

Additional tests were performed with the needle and FBG oriented inwards towards the tube with a non-orthogonal angle of incidence between the needle and tube (FIG. 4B). Here, the needle was inserted at varying incident angles to the tube and pulled backwards for up to 12 mm. Measurements were made at displacements of 0.5, 5.0, 10.0, and 12.0 mm. Specifically, the needle was inserted at a 60 degree angle with respect to the length of the tube and rotated in three orientations (upwards, towards tube, and downwards). The data indicated an overall drop in signal magnitude due to an increased distance of the FBG away from the tube (FIG. 8: FBG directly faced the tube; average peak is 0.00526±0.0011 nm (n=15);

FIG. 9: FBG faced downwards; average peak: −0.00126±0.0003 nm (n=15); FIG. 10: FBG faced upwards; average peak: 0.003932±0.0006 nm. (n=15)). Directions such as "up" and "in" are more clearly evident when viewing, for example, FIG. 16.

Figure 11:
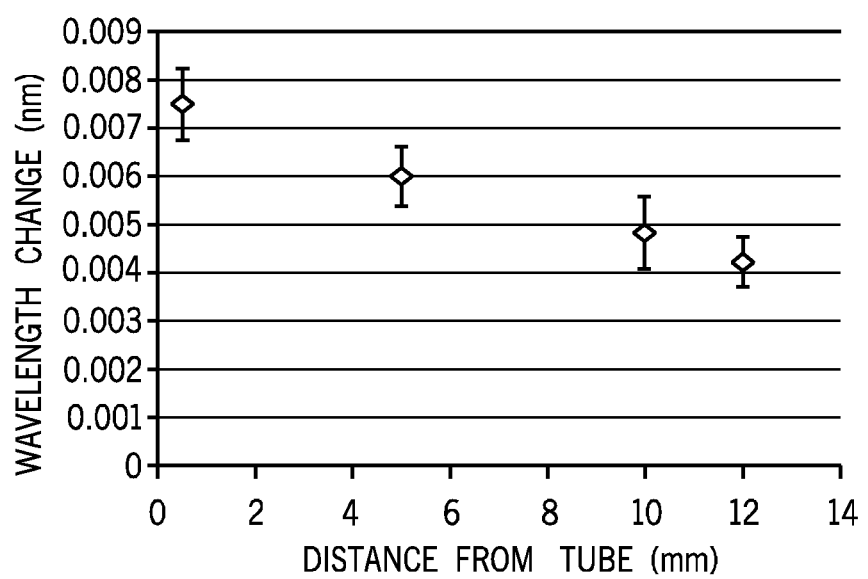
FIGS. 11-13 depict determining vessel location in an embodiment of the invention.
Figure 12:
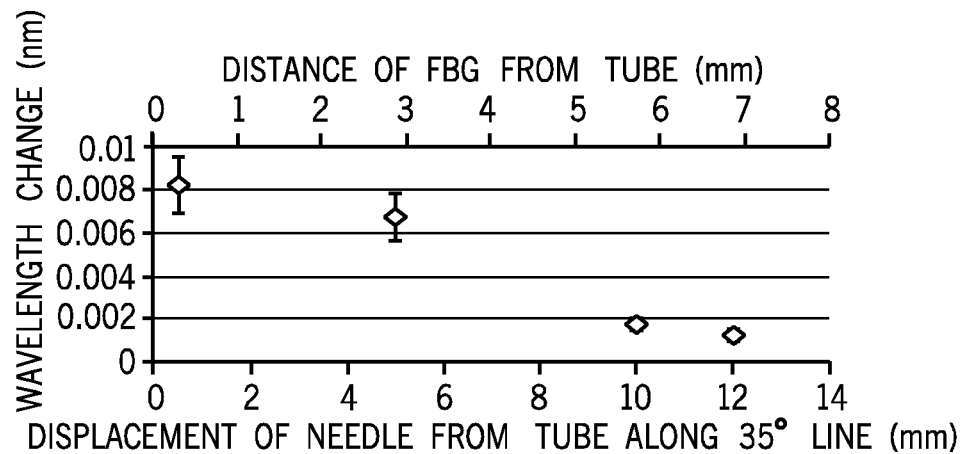
Figure 13:
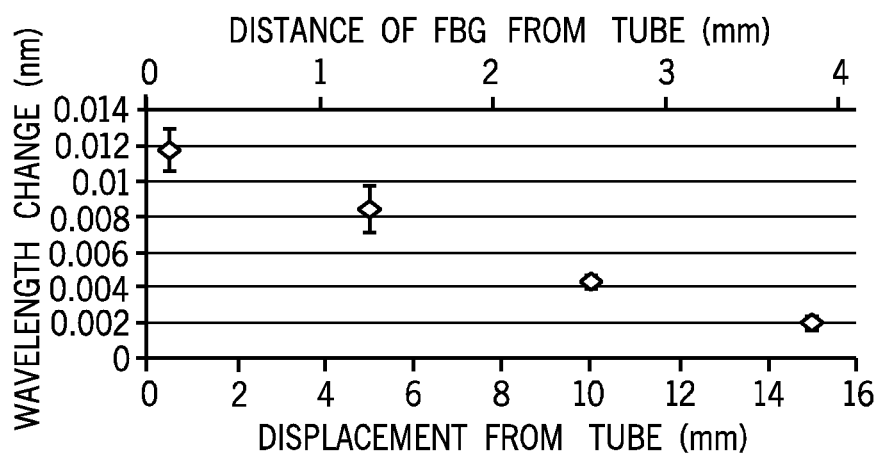

For distance testing in FIGS. 4-10, the signal magnitude dropped with increasing distance between the tube and FBG. Furthermore, the relationship between signal magnitude and distance was mostly linear for all cases (FIGS. 11-13). Note that in FIGS. 11-13 the displacement (x axis) refers to how much the needle was pulled out, and the actual distance of the FBG from the tube is smaller (e.g., indicated on secondary x-axis above graph; obtained by displacement times the sine of the angle) than how much the needle was pulled out. Specifically, in FIG. 11 the FBG was underneath and faced the tube. The signal dropped in correlation to increasing distance (15 measurements for each point). In FIG. 12 the FBG faced inwards towards the tube as the needle was inserted about 33° from the tube. Signal magnitude dropped with increasing displacement (15 measurements for each point). In FIG. 13 the FBG faced inwards towards the tube as the needle was inserted 15° from the tube. Signal magnitude dropped with increasing displacement (15 measurements for each point).

Thus, as seen above, embodiments can detect increasing stresses with the sensor based on decreasing the angle of incidence between the vessel and the first optical sensing stress sensor. For example, from FIGS. 5-7 the maximum signal magnitude was recorded when the FBG faced directly at the tube (low angle of incidence with respect to normal axis). Assuming that this magnitude is the largest for any place around needle cross section, then this value can be normalized to 1. Returning to the convention set earlier ($\theta=0°$ is the angular position in which the pulse impacts the needle), then the value of 1 corresponds to angle $\theta=0°$ for a cosine distribution. The maximum positive value occurs at the angle of impact, and decreases into the negative maximum at the opposite side (FIG. 14).

Figure 14:
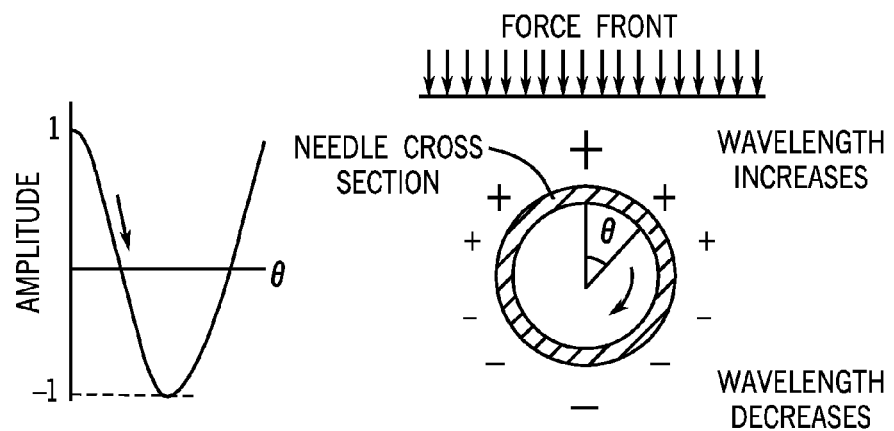
FIG. 14 includes an embodiment of the invention.

In FIG. 14, for deflection of the needle in one direction, a cosine-distribution strain field around the circumference of the needle is experienced by the FBGs. In an embodiment, the closer the FBG is to the angle of impact, the higher and more positive the wavelength change will be. In FIG. 14 the angle of impact is set to $\theta=0°$, which corresponds to the maximum positive value in a cosine distribution. For convenience, the angular position around the needle cross section experiencing the largest positive change is set as 0°. This location does not necessarily correspond to the location of an FBG. When the FBG is facing the tube (0° to tube), the average peak (nm) is 0.0153±0.0048 (n=15), the normalized average is 1, and the calculated angle is 0°. When the FBG is facing sideways (90° to tube), the average peak (nm) is −0.0058±0.0032 (n=18), the normalized average is −0.380±0.2409, and the calculated angle is 112.3±16.05°. When the FBG is facing away (180° to tube), the average peak (nm) is −0.0144±0.0031(n=16), the normalized average is −0.942±0.3593, and the calculated angle is 160.3±34.66°. The angle was calculated by taking the inverse cosine of the normalized value.

As seen above, the calculated angles indicate the other two orientations were not at their ideal positions. Each was approximately 20° off, although the actual average of the second and third FBG falls within the statistical range for being at their ideal locations. This may also mean that the maximum signal was close to but not actually at the 0° orientation, thus contributing error in the calculated results. Furthermore, the shearing forces between the FBG and the tissue may contribute a bias to the reading. Perhaps the largest source of error is generated from the manual compression of the pump, thus causing variable force to be exerted upon the needle.

Figure 8:
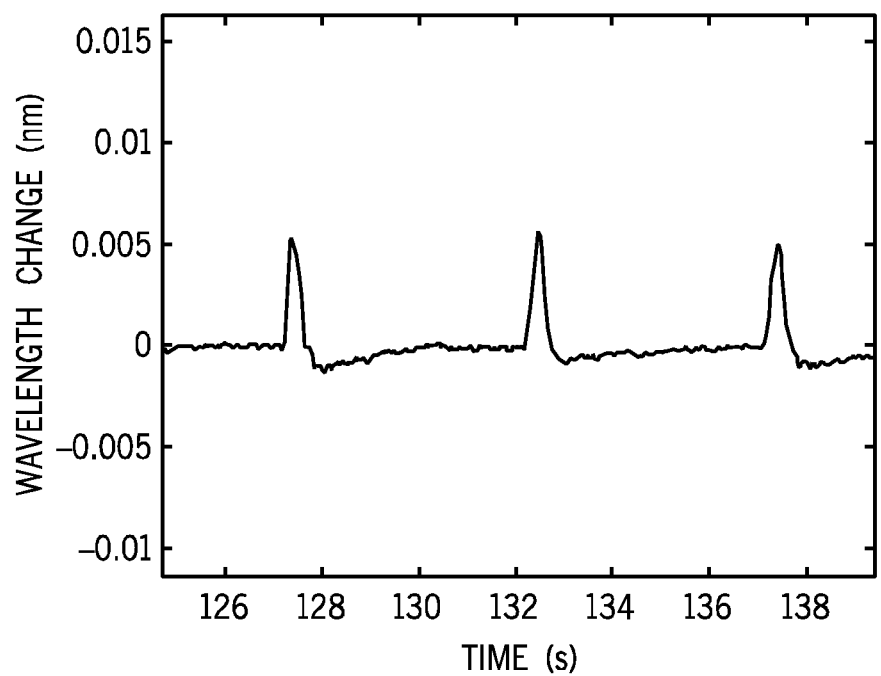
FIGS. 8-10 depict determining vessel location in an embodiment of the invention.

Regarding FIGS. 8-10, the needle was inserted at an angle and thus in an embodiment there is lower certainty regarding which FBG reading corresponds to the largest value; the normalization method used to calculate the angles in the first case may not be used in the second case. However, from FIGS. 5-7 a cosine distribution can be assumed. Then using the average peak values of data taken from two positions that are not 180° apart, the cosine distribution can be approximated (assuming a cosine distribution, two points that are 180° apart will give identical measurements) (FIG. 15).

Figure 15:
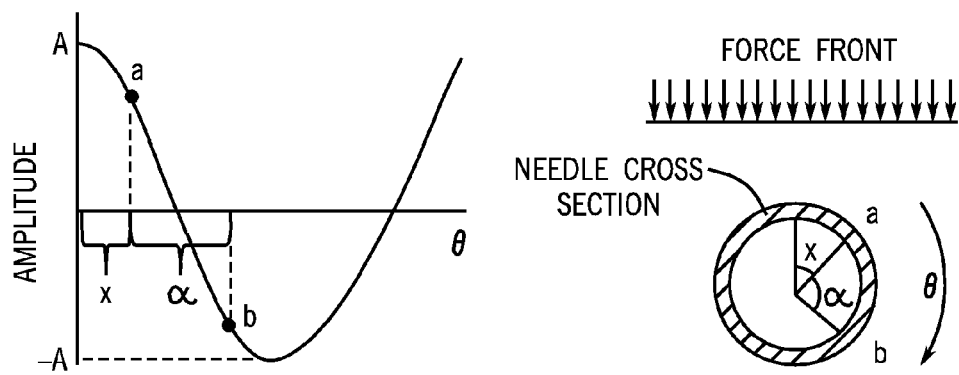
FIGS. 15-16 include multi-sensor embodiments of the invention.

In FIG. 15, for two FBGs that do not have an angular distance of 180° between each other their readings can be used to determine the source direction of an impacting force. The values of a, b, and $\alpha$ are known. Points a and b represent the locations and readings of two FBGs that are $\alpha$ degrees apart on the circumference of the needle cross section. The angular distance from the FBG at point a to the location of impact is labeled as x. The maximum positive point is at $\theta=0°$. Point a is x degrees away from the maximum point. Thus, determining x may indicate the direction of the artery. Each point along the cosine curve can be expressed as $$p = A\cos(\theta), \tag{1}$$

where p is the value of the point, A is the amplitude of the curve, and $\theta$ is the angular position of the point. Thus, points a and b can be respectively described by $$a = A\cos(x), \tag{2}$$

and $$b = A\cos(x+\alpha). \tag{3}$$

Their ratio $\beta$ can be taken to cancel the amplitude A, $$\beta = \frac{\cos(x)}{\cos(x+\alpha)}. \tag{4}$$

The denominator can be moved to the left $$\beta\cos(x+\alpha) = \cos(x), \tag{5}$$

then by using a trigonometric identity, the expression can be rewritten as $$\beta[\cos(x)\cos(\alpha) - \sin(\alpha)\sin(x)] = \cos(x). \tag{6}$$

The variable x can be isolated and solved in the following algebraic manipulations:

$$-\beta\sin(\alpha)\sin(x) = \cos(x) - \beta\cos(x)\cos(\alpha) \tag{7}$$

$$-\beta\sin(\alpha)\sin(x) = \cos(x)(1 - \beta\cos(x)\cos(\alpha)) \tag{8}$$

$$\frac{\sin(x)}{\cos(x)} = \frac{\beta\cos(\alpha) - 1}{\beta\sin(\alpha)} \tag{9}$$

Since $\sin(x)/\cos(x)$ is $\tan(x)$, then x can be expressed as the following equation of known values:

$$x = \tan^{-1}\left[\frac{\beta\cos(\alpha) - 1}{\beta\sin(\alpha)}\right]. \tag{10}$$

The average peak values can be used as points along the cosine curve. Each value is assumed to have an ideal 90° (thus, α=90°) angular separation. Points that are 180° apart may have equal magnitude, and thus may not be independent values in an embodiment. In an embodiment points less or greater than 180° apart will produce signals that can be used to calculate the direction of the force. In FIGS. 8-10 the viable combinations of FBGs are "facing inwards"/"facing up", and "facing inwards"/"facing down" as these combinations do not have FBGs that are simultaneously 180° away from each other. With "In"/"Up" α=90°, β=1.338±0.2830; and x=−36.78±0.1014°. With "In"/"Down" α=−90°, β=−4.188±0.8974; and x=−13.43±0.0484°. From the "In"/"Up" combination, the maximum signal and thus the direction of the artery could be reached by rotating the inward facing FBG by −36.78°. From this result, the needle was actually at a lower altitude relative to the pulsating tube.

Figure 16:
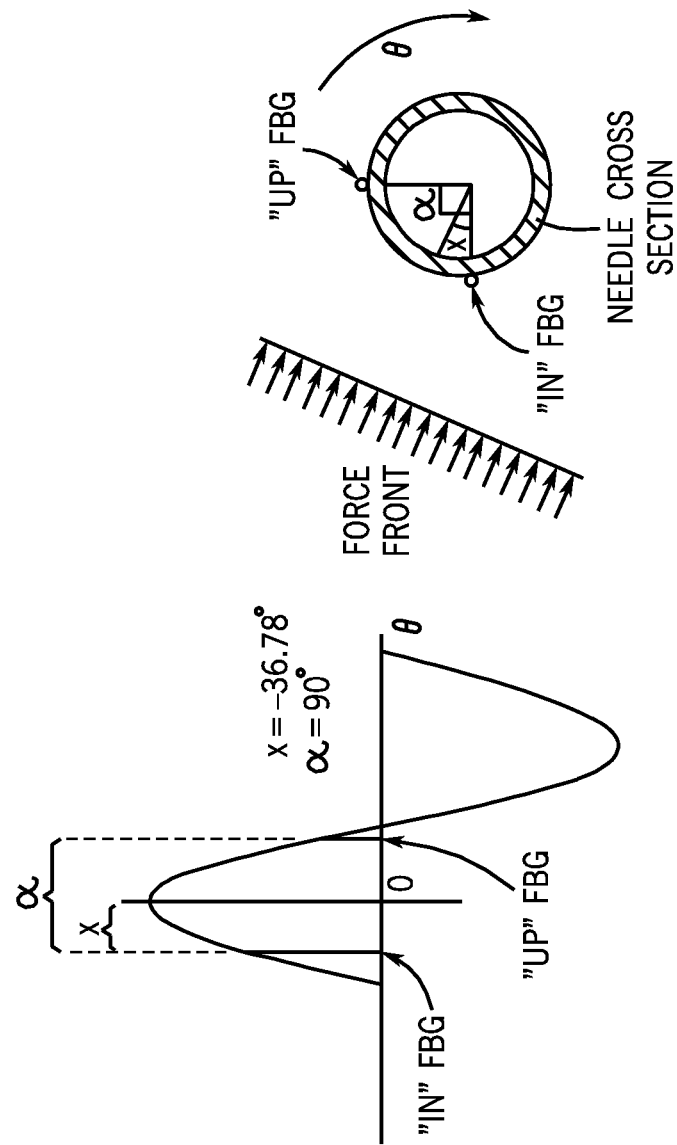

FIG. 16 illustrates the calculated results on a cosine wave function and the corresponding location on the needle circumference. Calculating the angular position of an incoming force based on data from the second case (i.e., FIGS. 8-10). The "In" FBG faced inwards towards the tube, and the "Up" FBG faced upwards (90° angular distance away from the "In" FBG) with respect to the global coordinates. From the known values, the calculated location of impact was located 36.78° above the "In" FBG. Using the other combination, an angle of −13.43° was calculated. This value indicated the inward facing FBG was closer to the angular position of the impacting force than was calculated with the previous value.

Errors in these calculations are due mainly to the assumption that the FBGs are perfectly 90° apart. Shear forces between the FBG and the tissues also contribute to extra signals. Simultaneous use of two FBGs installed precisely at a distance apart from each other will significantly reduce the uncertainty in the measurements and calculations. On the other hand, the results correctly indicated the direction of the tube. This ability is useful in cases where the operator does not have visual confirmation of the vascular structures in question.

The distance testing indicated a fairly linear relationship between the distances of the needle and the amplitude of signals generated by the FBG. During the experiment for one embodiment, it was observed that when the FBG was within the tissue, signals due to the pulsating tube were generated. However, the seemingly linear drop in signal with increasing distance suggests that after a certain distance, no or fewer signals may be observed. For example, a linear fit of FIG. 11 indicates that after 25 mm, all relevant signals will be diminished. For the datasets in FIGS. 12-13, the drop in signal was much steeper per displacement (linear fit indicates less than 16 mm for the range of detection). This difference may be explained by the length of needle inserted inside the tissue during these tests. In FIG. 11, the needle was brought to the same depth within tissue for each reinsertion. Conversely, in FIGS. 12-13, where the needle was pulled outwards to create additional distance from the tube, the insertion length decreased for increased distances. Thus, less of the needle's surface area was exposed to the vibrations, contributing to the decrease in signal. Since needle insertions are mostly done at an angle, the indicated 16 mm range is more realistic for the actual range of the FBG needle.

In FIGS. 12-13, a secondary axis located on top of the graph represented the direct distance of the FBG from the tube, and is much smaller than the displacement of the tube. However, this number may not signify the functional range of the needle as the needle will travel much more before contacting the tube (if the needle continued on its angled trajectory). These results may show the FBG needle is sensitive to the distance between itself and a pulsating source. However, various factors may affect results (e.g., tissue makeup, pulse strength, vessel elasticity, and instrument sensitivity).

Figure 1B:
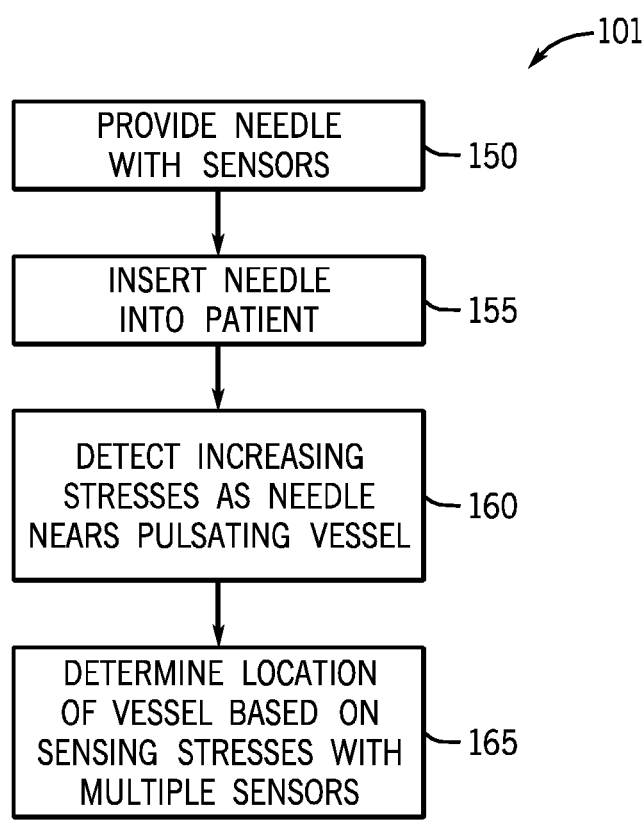

Thus, FIG. 1B includes method 101 in an embodiment of the invention. Block 150 provides a rigid hollow needle having an end portion coupled to a fiber optic cable, a light source, and first and second optical sensing stress sensors (see FIG. 15, points A and B). In block 155 a user inserts an end portion of the needle into a patient having a pulsating blood vessel (e.g., artery). Light is provided from the light source to FOC 215 and the user advances the end portion towards the pulsating blood vessel. In block 160 the device detects first increasing stresses, over a multi-second time period (e.g., time period it takes to puncture skin, move end portion near target vessel, and puncture target vessel) and in substantially real-time, based on both advancing the end portion towards the pulsating blood vessel and optically sensing with the with first optical sensing stress sensor (e.g., sensor A of FIG. 15).

Furthermore, still in block 160, the system or device detects second increasing stresses, over the multi-second time period and in substantially real-time, with the second optical sensing stress sensor based on advancing the end portion towards the first pulsating blood vessel. In block 165, the system determine the detected first increasing stresses are unequal to the detected second increasing stresses (where the first and second optical sensing stress sensors are radially displaced from one another by less than 180 degrees) and determines the location of the first pulsating blood vessel based on determining the first and second increasing stresses.

In an embodiment, block 165 may include determining an angle of rotation, about the needle's major axis, between the first optical sensing stress sensor and the first pulsating blood vessel.

Also, in an embodiment the first optical sensing stress sensor may be coupled to the needle distal to the second optical sensing stress sensor. In such an embodiment, block 165 may include detecting the end portion of the needle pierced the first pulsating blood vessel based on the first optical sensing stress sensor being coupled to the needle distal to the second optical sensing stress sensor. Thus, installation of sensors (e.g., FBGs) in strategic places along the needle may allow a coupled computing system to calculate the direction of the vibration source, and hence the localization of an artery.

As mentioned above, various embodiments include methods and systems for detecting increasing stresses. Doing so may include detecting a first stress based on a first pulse from the first pulsating blood vessel and detecting a second stress based on a second pulse from the first pulsating blood vessel, where the first stress is unequal to the second stress.

In an embodiment, the vessel may be located based on readings from a single sensor (wherein the device includes multiple sensors or just the one sensor). The vessel may be located by rotating the needle about its major axis; detecting first increasing stresses at one position and then second increasing stresses at the newly rotated position; and then advancing the end portion towards the first pulsating blood vessel based on detecting the second increasing stresses are greater than the first increasing stresses.

In an embodiment, the system will not only allow detection of the vessel but may also guide the operator in the direction of the vessel by providing real-time audio and visual feedback based on the signal alterations during maneuvering of the needle. For example, as shown above the orientation of the vessel in relation to either one or multiple sensors is obtainable. From that point the desired direction for the end portion to be moved may be given orally, visually (e.g., LED on needle handle illuminating green when moving towards the vessel, a monitor screen with a depiction of the needle and an indicator illustrating the portion of the needle closest to the vessel, and the like) and tactilely (e.g., vibration when moving away from the vessel).

For example, an embodiment includes a method for informing the operator the direction of the blood vessel based on the measurements. If the needle was inserted at random rotations each time, then the instructions to turn or steer a certain direction may not be substantial to the operator. The operator may not have a reference point to turn or steer from. On the other hand, if each FBG were labeled (e.g., numbers, colors, lights, etc.), then prompts can be made that instruct the operator to move the needle a certain distance with respect to one of the FBGs.

Gathering data (see above) showed two events contributed to the signals read by the FBGs. One event was deflection of the needle due to incoming forces, and the other was the shear between the FBG and the needle. The cosine distribution should vary in magnitude depending on the yaw and pitch of the needle in relation to the length of the tube. As the needle becomes more parallel to the tube, the signals should be fairly strong and the calculations would clearly indicate a direction. Conversely, as the needle becomes increasingly perpendicular to the tube (while still directly pointing at it as opposed to going underneath), the signals may be predominantly generated by shear and compression of the needle. Some or all of the calculations described earlier may not be able to provide a solution to determine the direction of impact. However, compression may cause all FBGs on the needle to reflect a shorter wavelength. However, detection of this phenomenon can be implemented in, for example, software such as by indicating when the signal drops below a certain threshold or if compression is seen across all FBGs.

An embodiment may alert the operator when the needle penetrates a vessel. The puncture of a vessel may be identified by two major events. One of these events is traversion through the vessel wall. Transition into the stiffer and tensed vessel wall (as compared to surrounding tissue) may initially magnify the magnitudes of existing signals, followed by relaxation as the needle passes the vessel wall. The increased magnitude is also important because despite the ability of the FBG needle to sense distance, an embodiment may not know the distance before the needle contacts the vessel. The magnification of signals may be large enough to warrant special attention, and thus can be a sign that the needle tip has reached a vessel wall. This event may be more pronounced for patients with stiffer blood vessels, such as diabetics. The second event is the effect of pulsatile blood flow on the needle. During this event, the FBG may detect localized stress concentrations due to blood flow in addition to the deflections of the needle. Minor flow induced vibrations may also be present. The signal pattern generated by the FBG sensors during this event will differ significantly from before. As the blood flow in vein and artery are dissimilar, the operator will also be able to tell which type of vascular structure was penetrated based on the different signal profile generated by the FBG needle.

Other embodiments of the FBG sensorized needle may embed the FBGs into the needle and have an exact, known angular displacement between two FBGs. By embedding the FBG into the needle, shear forces may be minimized, and the FBG may sense strains coming mainly from the deflections of the needle. Various options are available for embedding FBG cables into the needle. One method may create the conduits during the extrusion of the needle during the manufacturing process. The outer and inner surfaces of the needle will remain identical to conventional vascular needles, but holes will be present in the wall of the needle. Placement of FBG may become difficult as the FBG needs to be threaded through the hole without being damaged. Another method is to cut trenches along the length of the needle. Each trench is deep enough to completely contain the FBG and still have some clearance between the FBG and the outer surface level of the needle's wall. The clearance is then filled up with a sealing material such as epoxy and polished. In either method, the passageways containing the FBGs may need to be precisely placed apart. However, in various embodiments the angular distance between two FBGs (if only two are used) may not be equal to 180° as this may create redundant information that may not be used to sense the direction of an artery.

In an embodiment, two or more coplanar sensors (e.g., FBGs or piezoelectric sensors) may be used per needle. Additional FBGs in the same plane may provide more precise and accurate measurements. As mentioned herein, an embodiment may sense when a vessel has been penetrated. One indication of vessel puncture is the presence of local blood flow around invading part of the needle. That part of the needle is likely the tip of the needle, which contains the FBGs. Thus, by installing an FBG a distance before the main FBGs, these local events can be better isolated (i.e., the outlying FBG will sense mainly the deflections of the needle while the immersed FBGs at the tip will be confronted with effects of local blood flow).

An embodiment may be able to differentiate between veins and arteries (or between any two vessels of differing pressures) based on the strength of the respective pulses (and consequent wavelength shifts). For example, if a user knows the needle is adjacent a vessel but is unsure whether the vessel is a vein or artery, the magnitude of wavelength change may indicate whether the target vessel is a vein or artery.

While several embodiments are described in terms of vascular access (arterial, venous, and all other vascular components are applicable to embodiments of the invention), other embodiments are applicable to providing the operator with guidance when using any manner of a needle-type device to access various body structures or organs. Examples include when the structure is marked by the movement of gas or fluids (e.g., ducts, airways) that are capable of generating the stress waves for the needle device to sense.

Also, while many embodiments have been addressed with respect to optical sensors and FBG sensors (which provide advantages over certain electrical sensors that are prone to electronic noise issues), other embodiments are not necessarily limited to FBGs or even to optical sensors. As mentioned herein, in some capacities piezoelectric sensors may have some applications but not necessarily all applications discussed herein.

Figure 17:
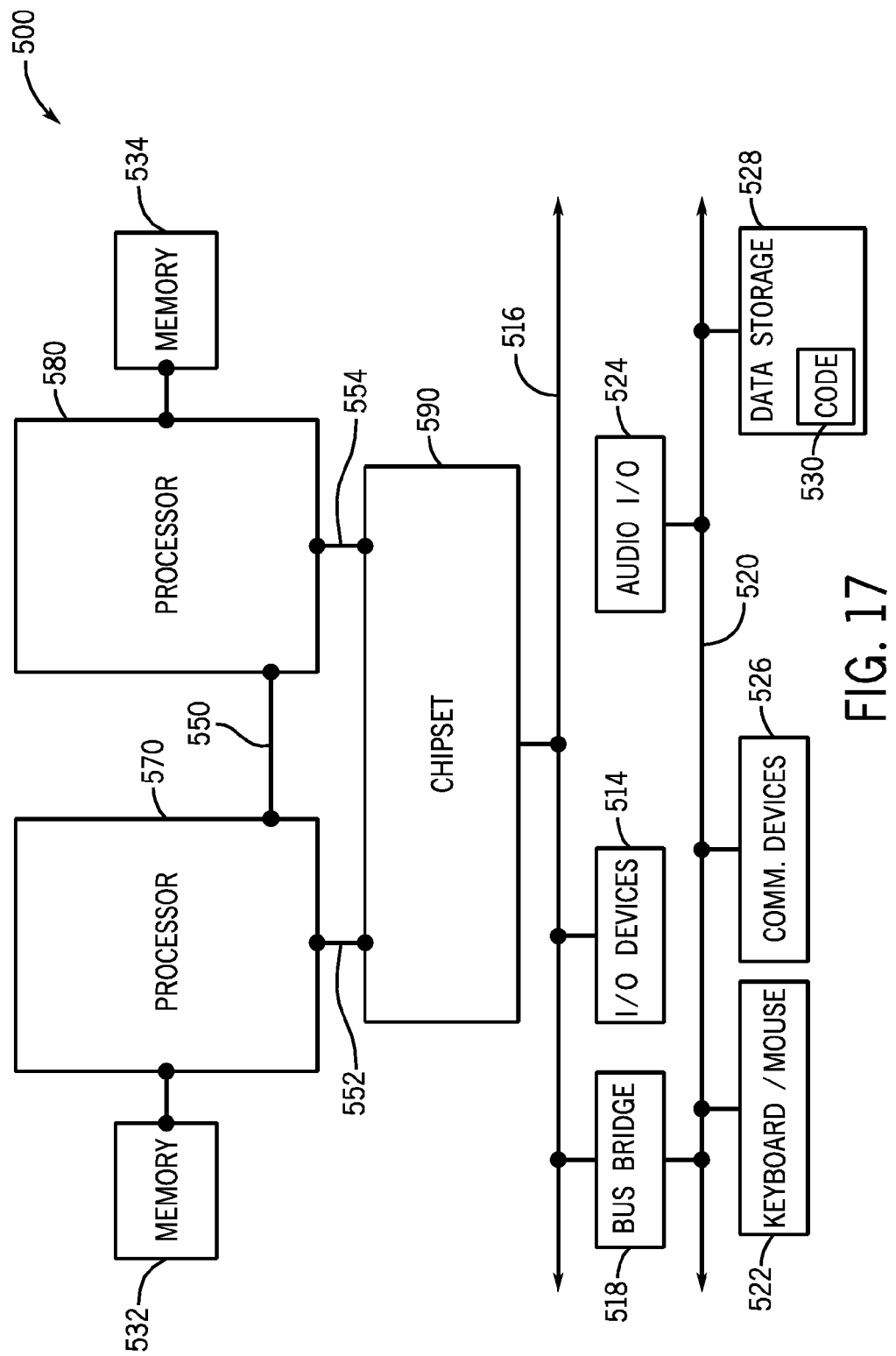
FIG. 17 includes a system for use with embodiments of the invention.

Embodiments may be implemented in many different system types. Referring now to the FIG. 17, shown is a block diagram of a system in accordance with an embodiment of the present invention. Multiprocessor system 500 is a point-to-point interconnect system, and includes a first processor 570 and a second processor 580 coupled via a point-to-point interconnect 550. Each of processors 570 and 580 may be multi-core processors. The term "processor" may refer to any device or portion of a device that processes electronic data from registers and/or memory to transform that electronic data into other electronic data that may be stored in registers and/or memory.

First processor 570 may include a memory controller hub and point-to-point (P-P) interfaces. Similarly, second processor 580 may include a MCH and P-P interfaces. The MCHs may couple the processors to respective memories, namely a memory 532 and a memory 534, which may be portions of main memory (e.g., a dynamic random access memory (DRAM)) locally attached to the respective processors. First processor 570 and second processor 580 may be coupled to a chipset 590 via P-P interconnects, respectively. Chipset 590 may include P-P interfaces.

Furthermore, chipset 590 may be coupled to a first bus 516 via an interface. Various input/output (I/O) devices 514 may be coupled to first bus 516, along with a bus bridge 518, which couples first bus 516 to a second bus 520. Various devices may be coupled to second bus 520 including, for example, a keyboard/mouse 522, communication devices 526, and data storage unit 528 such as a disk drive or other mass storage device, which may include code 530, in one embodiment. Further, an audio I/O 524 may be coupled to second bus 520.

Embodiments may be implemented in code and may be stored on a storage medium having stored thereon instructions which can be used to program a system to perform the instructions. The storage medium may include, but is not limited to, any type of disk including floppy disks, optical disks, optical disks, solid state drives (SSDs), compact disk read-only memories (CD-ROMs), compact disk rewritables (CD-RWs), and magneto-optical disks, semiconductor devices such as read-only memories (ROMs), random access memories (RAMs) such as dynamic random access memories (DRAMs), static random access memories (SRAMs), erasable programmable read-only memories (EPROMs), flash memories, electrically erasable programmable read-only memories (EEPROMs), magnetic or optical cards, or any other type of media suitable for storing electronic instructions.

Embodiments of the invention may be described herein with reference to data such as instructions, functions, procedures, data structures, application programs, configuration settings, code, and the like. When the data is accessed by a machine, the machine may respond by performing tasks, defining abstract data types, establishing low-level hardware contexts, and/or performing other operations, as described in greater detail herein. The data may be stored in volatile and/or non-volatile data storage. For purposes of this disclosure, the terms "code" or "program" cover a broad range of components and constructs, including applications, drivers, processes, routines, methods, modules, and subprograms. Thus, the terms "code" or "program" may be used to refer to any collection of instructions which, when executed by a processing system, performs a desired operation or operations. In addition, alternative embodiments may include processes that use fewer than all of the disclosed operations, processes that use additional operations, processes that use the same operations in a different sequence, and processes in which the individual operations disclosed herein are combined, subdivided, or otherwise altered.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A method comprising:
providing a rigid hollow needle having an end portion coupled to a first fiber optic cable, a first light source, and a first optical sensing stress sensor, wherein the first optical sensing stress sensor includes a fiber Bragg grating (FBG);
inserting the end portion into a patient including a first pulsating blood vessel, wherein the fiber Bragg grating (FBG) aids guidance of the needle towards the first pulsating blood vessel for entry into the first pulsating blood vessel;
providing light from the first light source to the first fiber optic cable;
monitoring a signal from the first fiber optic cable to detect stress with the first optical sensing stress sensor over a multi-second time period and in substantially real-time, wherein the stress that is detected is monitored for first increasing stresses resulting from said first pulsating blood vessel; and
advancing the end portion towards a direction of the first pulsating blood vessel in accordance with the first increasing stresses, wherein an increase in the stress detected by the first optical sensing stress sensor during advancement indicates the direction of the first pulsating blood vessel.

2. The method of claim 1, wherein the rigid hollow needle is selected from the group consisting of a hypodermic needle, trocar, catheter, dilator, and sheath.

3. The method of claim 2, wherein the first increasing stresses increases as the end portion is advanced towards the first pulsating blood vessel.

4. The method of claim 3, including:
adjusting the rigid hollow needle to adjust an angle of incidence between an axis normal to the first pulsating blood vessel and the first optical sensing stress sensor;
monitoring the stress during the adjusting of the angle of incidence for second increasing stresses resulting from said first pulsating blood vessel with the first optical sensing stress sensor, wherein the second increasing stresses detected by the first optical sensing stress sensor are based on decreasing the angle of incidence between the axis normal to the first pulsating blood vessel and the first optical sensing stress sensor; and
advancing the end portion towards the direction of the first pulsating blood vessel in accordance with detecting the second increasing stresses, wherein the second increasing stresses indicating the direction of the first pulsating blood vessel.

5. The method of claim 1, wherein the rigid hollow needle has the end portion coupled to a second fiber optic cable and a second optical sensing stress sensor, and the first optical sensing stress sensor and the second optical sensing stress sensors are radially displaced from one another by less than 180 degrees; and
the method further includes detecting second stress with the second optical sensing stress sensor over the multi-second time period and in substantially real-time, wherein the second stress that is detected is monitored for third increasing stresses resulting from said first pulsating blood vessel; and
advancing the end portion towards the direction of the first pulsating blood vessel in accordance with the third increasing stresses, wherein the third increasing stresses detected by the second optical sensing stress sensor indicates the direction of the first pulsating blood vessel.

6. The method of claim 5 including determining the direction of the first pulsating blood vessel based on the first increasing stresses and the second increasing stresses detected by the first optical sensing stress sensor and the second optical sensing stress sensors.

7. The method of claim 5 including determining an angle of rotation, about a major axis of said rigid hollow needle, between the first optical sensing stress sensor and an impacting force from the first pulsating blood vessel.

8. The method of claim 5, wherein the first optical sensing stress sensor is coupled to the rigid hollow needle distal to the second optical sensing stress sensor; and
the method further including detecting the end portion piercing the first pulsating blood vessel based on the first optical sensing stress sensor being coupled to the rigid hollow needle distal to the second optical sensing stress sensor.

9. The method of claim 8, wherein the first optical sensing stress sensor differentiates whether the first pulsating blood vessel is a vein or artery based on a signal profile generated.

10. The method of claim 1, wherein the rigid hollow needle includes a channel along the length of the rigid hollow needle and the first fiber optic cable and the first optical sensing stress sensor are both included in the channel.

11. The method of claim 1 including:
rotating the rigid hollow needle about its major axis;
monitoring the stress detected by the first optical sensing stress sensor for fourth increasing stresses from the first pulsating blood vessel, over a multi-second time period and in substantially real-time, based on rotating the rigid hollow needle about its major axis; and
advancing the end portion in the direction of the first pulsating blood vessel based on the fourth increasing stresses, wherein the fourth increasing stresses detected by the first optical sensing stress sensor indicates the direction of the first pulsating blood vessel when an angle of rotation between the first optical stress sensor and an impacting force from the first pulsating blood vessel decreases.

12. A system comprising:
a first optical sensing stress sensor; and
a rigid hollow needle having an end portion to couple to a first fiber optic cable, a first light source, and the first optical sensing stress sensor, wherein the first optical sensing stress sensor includes a fiber Bragg grating (FBG) that aids guidance of the rigid hollow needle towards the first pulsating blood vessel for entry into the first pulsating blood vessel;
wherein when the end portion is inserted into a patient including a first pulsating blood vessel, light is provided from the first light source to the first fiber optic cable, and the end portion is advanced towards a direction of the first pulsating blood vessel;
the system is operable to monitor detected stress with the first optical sensing stress sensor over a multi-second time period and in substantially real-time; and
a microprocessor system evaluates the stress detected by the first optical sensing stress sensor for first increasing stresses, wherein the microprocessor system informs an operator of the direction of the first pulsating blood vessel based on both advancement of the end portion towards the first pulsating blood vessel and detection of the first increasing stresses, wherein an increase in the stress detected by the first optical sensing stress sensor during advancement indicates the direction of the first pulsating blood vessel.

13. The system of claim 12, wherein the rigid hollow needle is selected from the group consisting of a hypodermic needle, trocar, catheter, dilator, and sheath.

14. The system of claim 13, wherein said first optical sensing stress sensor detects increases in the first increasing stresses as the end portion is advanced towards the first pulsating blood vessel.

15. The system of claim 12 including:
a second fiber optic cable;
a second optical sensing stress sensor to couple to the rigid hollow needle and to the second fiber optic cable; and
wherein when the end portion is inserted into the patient, light is provided to the second fiber optic cable, and the end portion is advanced towards the first pulsating blood vessel;
the system is operable to monitor second stress with the second optical sensing stress sensor, over a multi-second time period and in substantially real-time;
wherein the first optical sensing stress sensor and the second optical sensing stress sensors are radially displaced from one another by less than 180 degrees; and
the microprocessor system evaluates the second stress detected by the second optical sensing stress sensor for the second increasing stresses, wherein the microprocessor system informs the operator of the direction of the first pulsating blood vessel based on both advancement of the end portion towards the first pulsating blood vessel and detection of the second increasing stresses, wherein an increase in the second stress detected by the second optical sensing stress sensor during advancement indicates the direction of the first pulsating blood vessel.

16. The system of claim 15, wherein the system is operable to indicate the direction of the first pulsating blood vessel based on sensing the first increasing stresses and the second increasing stresses detected by the first optical sensing stress sensor and the second optical sensing stress sensors.

17. The system of claim 12, wherein the microprocessor system includes:
a memory, and
a processor, coupled to the memory, to determine the direction of the first pulsating blood vessel based on sensing the first increasing stresses.

18. An article comprising a non-transitory medium storing instructions that enable a processor-based system to:
detect stress using a first optical sensing stress sensor over a multi-second time period and in substantially real-time, wherein the stress that is detected is monitored for first increasing stresses resulting from a first pulsating blood vessel, and the first optical sensing stress sensor includes a fiber Bragg grating (FBG) that aids guidance of a rigid hollow needle towards the direction of the first pulsating blood vessel for entry into the first pulsating blood vessel;
wherein the rigid hollow needle is coupled to a first fiber optic cable, a first light source, and the first optical sensing stress sensor; and
instruct the processor-based system to evaluate the stress detected by the first optical sensing stress sensor, wherein an increase in the stress detected by the first optical sensing stress sensor during advancement indicates a direction of the first pulsating blood vessel, wherein further an operator is informed of the direction of the first pulsating blood vessel based on both advancement of the end portion towards the first pulsating blood vessel and detection of the first increasing stresses.

19. The article of claim 18 storing instructions that enable the processor-based system to detect increases in the first increasing stresses as the end portion is advanced towards the first pulsating blood vessel.

20. The article of claim 18 storing instructions that enable the processor-based system to determine the direction of the first pulsating blood vessel based on the first increasing stresses detected by the first optical sensing stress sensor.

* * * * *